US010337295B2

(12) United States Patent
Bailey et al.

(10) Patent No.: US 10,337,295 B2
(45) Date of Patent: Jul. 2, 2019

(54) METHODS TO DETERMINE COMPOSITE VIBRATION INDICES OF A DRILLING ASSEMBLY

(71) Applicants: Jeffrey R. Bailey, Houston, TX (US); Gregory S. Payette, Spring, TX (US); Benjamin J. Spivey, Houston, TX (US)

(72) Inventors: Jeffrey R. Bailey, Houston, TX (US); Gregory S. Payette, Spring, TX (US); Benjamin J. Spivey, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 179 days.

(21) Appl. No.: 15/388,723

(22) Filed: Dec. 22, 2016

(65) Prior Publication Data

US 2017/0183940 A1 Jun. 29, 2017

Related U.S. Application Data

(60) Provisional application No. 62/271,482, filed on Dec. 28, 2015.

(51) Int. Cl.
*G06F 17/50* (2006.01)
*E21B 41/00* (2006.01)
(Continued)

(52) U.S. Cl.
CPC .......... *E21B 41/0092* (2013.01); *E21B 7/00* (2013.01); *E21B 44/00* (2013.01); *E21B 45/00* (2013.01);
(Continued)

(58) Field of Classification Search
USPC ...................... 703/2, 18, 5; 702/13
See application file for complete search history.

(56) References Cited

U.S. PATENT DOCUMENTS 4,715,451 A 12/1987 Bseisu et al.
5,205,163 A 4/1993 Sananikone
(Continued)

OTHER PUBLICATIONS

Ertas et al., "Drillstring Mechanics Model for Surveillance, Root Cause Analysis, and Mitigation of Torsional and Axial Vibrations," SPE 163420, Mar. 5-7, 2013, pp. 1-14.
(Continued)

*Primary Examiner* — Thai Q Phan
(74) *Attorney, Agent, or Firm* — ExxonMobil Upstream Research Company-Law Department (57) ABSTRACT

A method to drill a borehole or wellbore through an earthen formation using a drill bit on a drillstring, comprising the steps of: selecting a frequency-domain dynamic model of a drilling assembly that describes the dynamic response of the drilling assembly to excitation at an excitation frequency for operating at a set of selected drilling parameters that include at least rotary speed and weight on bit; calculating a composite vibration index by combining calculated vibration indices for each excitation frequency with the spectral weighting factors for each of the drilling parameter partitions; displaying said composite vibration index for each of the drilling parameter partitions; selecting preferred drilling parameters based on the displayed results, and using the preferred drilling parameters to drill a borehole with the modeled drilling assembly.

10 Claims, 7 Drawing Sheets

(51) Int. Cl.
  *E21B 7/00* (2006.01)
  *E21B 45/00* (2006.01)
  *G01N 29/46* (2006.01)
  *E21B 44/00* (2006.01)
  *G01N 29/14* (2006.01)
  *G01N 29/44* (2006.01)

(52) U.S. Cl.
  CPC ......... *G01N 29/14* (2013.01); *G01N 29/4472* (2013.01); *G01N 29/46* (2013.01)

(56) References Cited

U.S. PATENT DOCUMENTS

| | | | |
|---|---|---|---|
| 5,402,677 A | 4/1995 | Paslay et al. | |
| 6,237,404 B1 | 5/2001 | Crary et al. | |
| 7,114,578 B2 | 10/2006 | Hutchinson | |
| 7,893,398 B2* | 2/2011 | Georgi | G01V 5/06 250/265 |
| 8,504,342 B2 | 8/2013 | Bailey et al. | |
| 8,589,136 B2 | 11/2013 | Ertas et al. | |
| 8,977,523 B2 | 3/2015 | Ertas et al. | |
| 9,008,972 B2* | 4/2015 | Imhof | G01V 1/32 702/13 |
| 9,483,586 B2 | 11/2016 | Bailey et al. | |
| 2010/0025574 A1* | 2/2010 | Georgi | G01V 5/06 250/261 |

OTHER PUBLICATIONS

Bailey, J. R. et al., "*Design Evolution of Drilling Tools to Mitigate Vibrations,*" SPE 163503, Dec. 2013, pp. 350-369.
Bailey, J. R. et al., "*Development and Application of a BHA Vibrations Model,*" IPTC 12737, Dec. 3-5, 2008, pp. 1-12.

* cited by examiner

| Harmonic | | 1 | 2 | 3 | 4 | 5 | 6 |
|---|---|---|---|---|---|---|---|
| Vibration Index | VI | 1.30 | 1.60 | 0.80 | 5.20 | 0.40 | 1.00 |
| Weighting Factor | WF | 1 | 1.1 | 0 | 0.6 | 0.3 | 0.4 |
| VI Contribution | WF*VI | 1.3 | 1.76 | 0 | 3.12 | 0.12 | 0.4 |

Composite Vibration Index = Sum(VI Contributions) = 6.7

CVI(i,j) = 6.7

| RPM | VI: 1X | VI: 2X | WF: 1X | WF: 2X | CVI |
|-----|--------|--------|--------|--------|-----|
| 80  | 16     | 4      | 0.5    | 0.5    | 10  |
| 100 | 12     | 2      | 0.5    | 0.5    | 7   |
| 120 | 8      | 3      | 0.5    | 0.5    | 5.5 |
| 140 | 6      | 5      | 0.5    | 0.5    | 5.5 |
| 160 | 4      | 6      | 0.5    | 0.5    | 5   |
| 180 | 3      | 4      | 0.5    | 0.5    | 3.5 |

METHODS TO DETERMINE COMPOSITE VIBRATION INDICES OF A DRILLING ASSEMBLY

CROSS REFERENCE TO RELATED APPLICATION

This application claims the priority and benefit of 62/271,482 filed Dec. 28, 2015 entitled, "Methods to Determine Composite Vibration Indices of a Drilling Assembly," the disclosure of which is incorporated herein in its entirety.

FIELD OF THE DISCLOSURE

The present invention describes a method for modeling and designing a drilling system that accounts for vibrations that may be experienced by the drilling system equipment. In particular, the present invention describes a method to utilize measured drilling data to model drill strings to enhance drilling rate of penetration, to reduce downhole equipment failure, to extend current tool durability, and/or to enhance overall drilling performance. The modeling of the drill strings may be used to enhance hydrocarbon recovery by drilling wells more efficiently.

BACKGROUND

Industry literature related to drilling vibration modeling includes teachings directed to forced vibration (induced excitation) frequency-domain computational models with excitation at two or more frequencies. Drilling performance metrics determined by these models include vibration index values that relate the system response to the system excitation. Vibration indices and related discussions are discussed in part, for example, in U.S. Pat. No. 9,483,586 B2, U.S. Pat. No. 8,589,136 B2, and U.S. Pat. No. 8,977,523 B2. These models and disclosures do not inherently provide means to combine different excitation frequencies to represent a drilling operation.

Frequency-domain vibration models are computationally efficient and can be used to great benefit in drilling applications. For example there are many frequency-domain models in the literature for each of axial, lateral, and torsional vibrations. Different models have different boundary conditions, coupling, modes of vibration, element types, and so forth, but one common characteristic of linear forced vibration models is that the system excitation and response output occurs at the same frequency, and the output is linearly proportional to the input. In most cases, the amplitude of the input excitation is arbitrarily selected to be a reference value and may be constant for each excitation frequency.

Fourier analysis can be used to determine the frequency, or "spectral", content of a time series of data, and a complete description includes both real and imaginary parts, or equivalently magnitude and phase. Those skilled in the art appreciate how various windowing processes and averaging of spectral calculations applying Fourier analysis can be used to estimate a spectrum of a time series that may be longer than the duration of a single Fourier calculation. The "periodogram" function available in the MATLAB program from The MathWorks provides such functionality. This function calculates the amount of signal energy present at each frequency for an extended time series of data. These amplitude (or magnitude) factors provide quantitative information on the contribution of each frequency to the resulting signal.

In any design process, a greater number of different criteria increases the complexity of the selection process as it becomes increasingly difficult to meet all criteria as the number to be satisfied increases. It is simplest to have as few design criteria as possible that meet the design objectives. The cited frequency domain models do not inherently provide weighting of results according to magnitude, indeed the calculations typically assume a reference input value and provide system response for this input but do not specify the relative contributions of each frequency. Time domain modeling, though computationally intensive, does provide the combination of these components in the model output.

SUMMARY OF THE INVENTION

In light of the above considerations, there is a need in the industry for a method to reduce the dimensionality of the design process using frequency domain modeling by combining vibration indices for two or more excitation frequencies. A single vibration index that meaningfully represents the expected contributions of the two or more excitation frequencies to the actual drilling operation must represent the physics of the drilling process. In this way, the drilling dynamics considerations can be reduced to fewer selection criteria.

Continuous recording of high frequency data from commercial drilling tools and systems provides the capability to capture actual drilling measurements with sufficient data rates and resolution to enable high quality spectral analysis of drilling dynamics. These spectral datasets, determined by spectral analysis, provide information on the relative significance of the various vibration frequency components to the overall drill string vibration. There are multiple means to conduct spectral analysis known to those skilled in the art. Depending on the specific problem at hand, surface or downhole recordings may be appropriate.

There are many variables of interest in the drilling process, some of which are control variables and some of which are measured dependent variables, and some are both control variables with driller-determine setpoints that are subsequently measured at the rig and become measurements. These variables include but are not limited to: surface rotary speed, weight on bit (WOB), hook load, surface torque, drilling rate (or rate of penetration, ROP), calculated penetration per revolution (also known as depth of cut), drilling fluid pump pressure, fluid pump rate, mud pump strokes per minute, etc. During one operation, one set may be control variables, but in a different operation a different set may be the variables set by the driller. An exemplary but not exclusive set of drilling control parameters is surface rotary speed and weight on bit. Often when weight on bit is not used, the complementary control variable may be ROP or surface torque. Again, these are non-limiting exemplary drilling parameters.

When determining how to apply the spectral analysis to a given dataset, there are several possible choices to consider regarding how to determine the dataset that is used for a particular interval of drilling. It may be appropriate to consider all the data with a range of drilling parameters in one group, or partition, or it may be appropriate to divide the dataset into different partitions of data corresponding to several portions of the range of drilling parameters. In doing so, a specific result of the data processing may be representative of one portion of the dataset, with another result corresponding to a different input drilling parameter range. This partitioning of the drilling parameter space will be most readily explained in an example below.

Accordingly, the result of the spectral analysis includes one or more relationships between the drilling parameters and the frequency content of at least one measured drilling parameter. This spectral analysis then provides information regarding the relative significance of each frequency over a representative excitation range. These excitation frequencies may be used, with appropriate manipulations, in one or more lateral, torsional, or axial frequency domain models of a drilling assembly. In light of frequency-dependent model results and one or more datasets on the significance of the excitation frequencies to the drilling measurement, it is feasible to consider means to combine, via superposition, the vibration indices (VI) previously disclosed to obtain a novel composite vibration index (CVI) that weights the vibration indices according to the relative spectral content in the recorded datasets.

Such composite vibration indices may be more fully representative of the drilling process and thus provide better design criteria in view of the two or more excitation modes. For example, instead of the present design criteria to seek the BHA design with the lowest vibration indices at the fundamental 1× mode, the processed measurements may, for example, show that there is half as much data amplitude at the 2× harmonic mode, and perhaps amplitude at additional frequencies. Weights applied to the vibration indices should be related to the amplitudes of the two or more excitation frequencies of interest. In another implementation, contributions of the drilling rig mud pump systems may be considered with an excitation frequency related to the pump stroke rate and amplitude related to the spectral amplitude of the mud pump disturbance. The present design criteria does not formalize a process to assign weighting factors to the various excitation frequencies, and judgment is used to assess the relative importance of various modes, based largely on interpretation of field results. High frequency data measurements can be utilized to make the design process more quantitative.

The inventive method provides means to develop a composite vibration index (CVI) by application of appropriate weights to the model results comprising vibration indices determined for different excitation frequencies, wherein the CVI is based on the spectral content of data that is recorded, either downhole or at the surface, from a drilling rig operating a drilling assembly. Understanding the spectral content of measured data and calculating a Composite Vibration Index may provide better interpretation of frequency domain model results, thereby improving the operational guidance that may be provided to the driller.

BRIEF DESCRIPTION OF THE DRAWINGS

FIG. 1 is a normalized spectral response of lateral acceleration data from a measurement sub located near a drill bit, illustrating data from five different drill string surface rotary speeds. FIG. 1 also includes a partition map corresponding to the RPM-WOB drilling parameter space illustrating parameter ranges for each of five selected portions of the presented data.

DETAILED DESCRIPTION

Certain fundamental aspects of the art behind of the improvements disclosed herein are discussed in previous references, each of which is incorporated herein in its entirety and as needed to provided additional support for assuring comprehensive disclosure of the best mode for using the presently disclosed technology. One such exemplary incorporated disclosure is "Modeling and Designing of Well Drilling System That Accounts for Vibrations" (U.S. Pat. No. 9,483,586 B2, Bailey et al., 2016), provides for the calculation of bottomhole assembly lateral vibration performance metrics that depend on harmonics of the drill string rotary speed. In one implementation, a lateral excitation force is applied to the bit and the forced response of the bottomhole assembly to this excitation is calculated. Applications of this technology are published in certain SPE papers; see for example "Design Evolution of Drilling Tools to Mitigate Vibrations" (SPE 163503, Bailey et al., 2013).

"Methods and Systems for Mitigating Drilling Vibrations" (U.S. Pat. No. 8,589,136 B2, Ertas et al., 2013) and "Methods to Estimate Downhole Drilling Vibration Indices from Surface Measurement" (U.S. Pat. No. 8,977,523 B2, Ertas et al., 2015) describes similar vibration indices for axial and torsional vibration of the entire drill string. Implementations of these models include the application of forces and torques to the drilling assembly at various locations along the drill string, with calculation of the forced response of the assembly to these excitations in axial or torsional modes, or both. Exemplary applications of this technology are described in "Drillstring Mechanics Model for Surveillance, Root Cause Analysis, and Mitigation of Torsional and Axial Vibrations" (SPE 163420, Ertas et al., 2013).

An exemplary set of high frequency downhole data is also presented in "Development and Application of a BHA Vibrations Model", (IPTC 12737, Bailey et al., 2008). A portion of the exemplary data set presented therein is also included herein as FIG. 1 in this publication. Data graphs 100 present a normalized spectral response of lateral acceleration data from a measurement sub located near a drill bit, illustrating data from five different drill string surface rotary speeds. The horizontal axis is a normalized frequency comprised of the ratio of the spectral frequency divided by the rotary speed, expressed in the same units. Spikes at integral multiples ("harmonics") of the rotary speed may be seen in this chart.

The normalized spectra 100 of lateral acceleration data from a near-bit measurement sub shows the amplitude of the frequency response (or spectrum) of the lateral acceleration plotted against normalized frequency on the horizontal axis. The significance of the individual harmonics of the drill string rotary speed is illustrated by normalizing the spectral frequency (horizontal axis of the chart) by the drill string rotary speed and comparing results for various rotary speeds. Results are shown here at 51 RPM (110), 60.6 RPM (120), 76.8 RPM (130), 81.2 RPM (140), and 102.5 RPM (150). These are the average rotary speeds for all data determined to be within each of the five bins shown in the partition map 101 (lower portion of FIG. 1). Note that all data is considered to be in the same WOB bin, and there is no separate partitioning for bit weight in this example.

Figure 1:
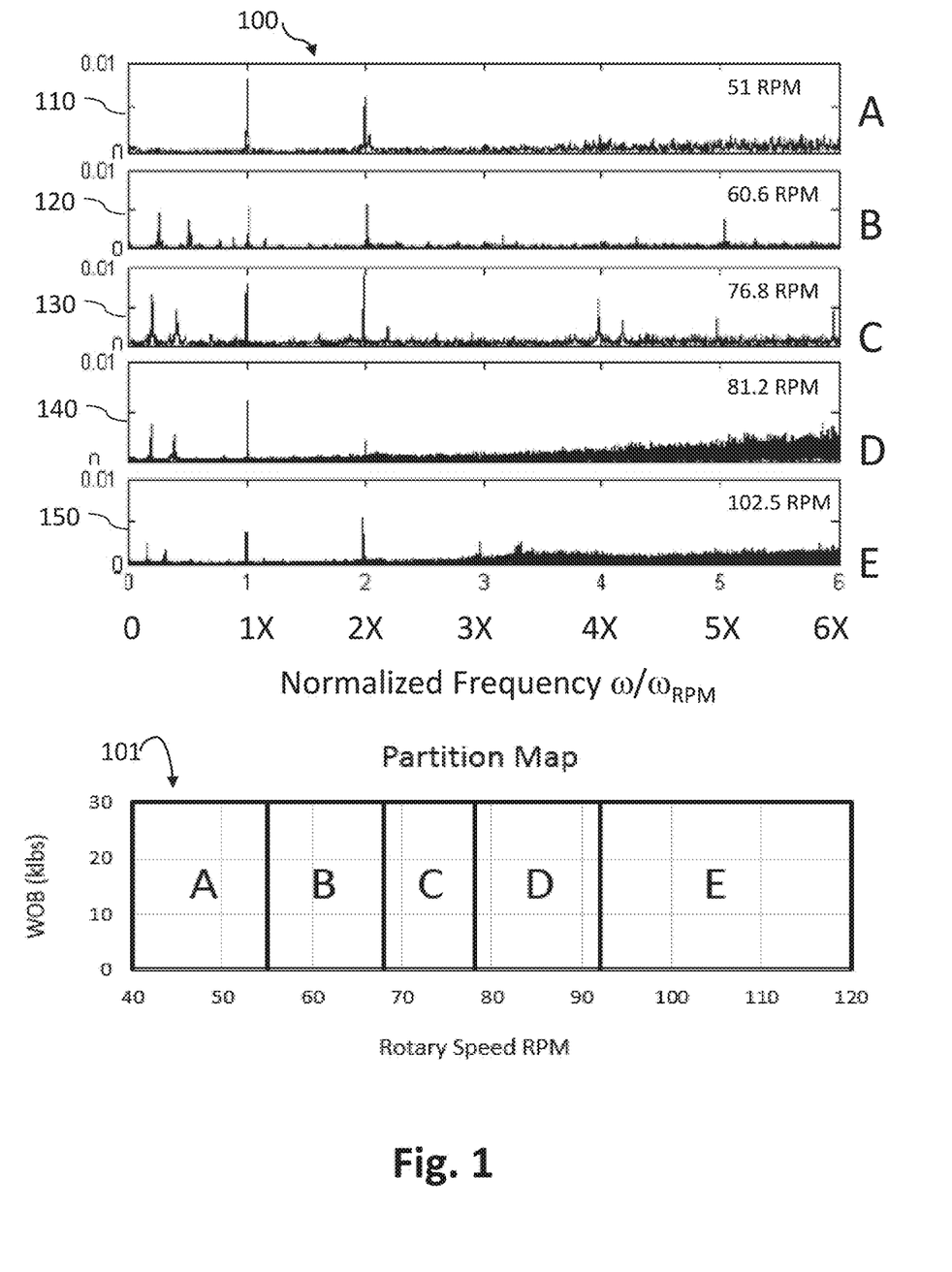

Significant peaks occur at multiples of the fundamental rotary speed of the drill string. The fundamental harmonics are identified at normalized frequency equal to 1.0; this is the synchronous mode at the rotary speed. This corresponds to the spike in each chart at the fundamental mode, or "1×" mode. One also see peaks at higher order harmonic multiples of the rotary speed. For example, there are spikes in each response at 2.0, the "2×" mode or second harmonic. There are also blips at some higher harmonics, as well as at non-harmonic frequencies. The peaks between normalized frequency of 0 and 1 are thought to be due to the rig mud pumps and are not self-induced by bottomhole assembly dynamics. These may be included in the formalism by inclusion of frequency bins at non-integral rotary speeds, or alternatively, by integrating over a continuous spectrum rather than summing over discrete frequency contributions.

Note that induced vibrational excitation of a drill string at multiples of the rotary speed has been known and discussed in industry literature for many years. However, this the time-consuming complexity in working with even the small dataset presented in FIG. 1 clearly illustrates the need for developing and value in having an improved quantitative understanding of the harmonic content of such data signals over significantly larger datasets, for example data taken over an entire bit run, or the length of a specific geologic formation that is known to damage downhole tools. Exemplary inquiries required for proper interpretation may include inquiries such as; "Is the 1× mode always present? How prevalent is the 2× mode? Can the 3× mode be discounted most of the time, or is it the most important factor (e.g. for roller cone bit bounce)? Is there significant energy at higher multiples? How do these results vary with selection of different drill bits, tools, bottomhole assembly design, etc.?" Quantitative calculations combining frequency spectra from measured data with model calculations as disclosed herein may provide solutions and answers, or at least certain information related to the analyzed data set. Furthermore, data from specific applications can be used to tune model results based on local field data, facilitating customization of results to local conditions, bit and tool selections, etc.

According to one aspect of the presently disclosed methods, recorded data from a dynamic measurement tool ("field measurements") are processed to determine the spectral content of at least one of a lateral vibration measurement, an axial vibration measurement, a torsional vibration measurement, a bending measurement, a rotary speed measurement, combinations or mathematical transforms thereof, or some other recording of drilling dynamics. Exemplary transforms include division of an acceleration spectrum by frequency to obtain a velocity spectrum, or division by frequency-squared to obtain a position spectrum. This data may be processed to determine for example, (for average or peak operating conditions, or both) the dominant spectral content of the field measurements for a specific operational environment, interval, or condition. This spectral information ("data") is used to weight the vibration model results ("model") to obtain a more representative or calibrated model result ("results").

In one non-limiting exemplary application or the presently disclose methods, the referenced lateral vibrations model is excited by a lateral force applied to the bit at multiples of the rotary speed. "Modeling and Designing of Well Drilling System That Accounts for Vibrations" (U.S. Pat. No. 9,483,586 B2, Bailey et al., 2016), discloses the calculation of vibration performance metrics that depend on harmonics of the drill string rotary speed. For excitation at each multiple of the rotary speed, model results are calculated to generate various vibration indices, one of which is the average dynamic bending strain energy in the bottomhole assembly. These multiples of the rotary speed are excitation frequencies, but in the most general case excitation may occur at additional frequencies. Therefore, vibration indices ("VI") are written as a function of the rotary speed (RPM), bit weight (WOB), and frequency $\omega$, as well as additional factors described in the references that have been incorporated in this application. Note that other drilling parameters may be used in lieu of RPM and WOB as may be appropriate. This may be written as, $$VI=VI(RPM, WOB, \omega) \qquad \text{(Eqn. 1)}$$

The five spectra of the data presented in FIG. 1 are illustrated, for example, with variability as a function of rotary speed for the drilling equipment at surface, wherein each portion of the figure is determined for a different rotary speed partition. The data provided is for the entire bit weight data range recorded at the time, so there is essentially one WOB partition. Data point 110 corresponds to drilling data within an interval about 51 RPM, and data point 120 refers to a data range about 60.6 RPM, and so on. In the most general case, the spectra of a field measurement time series may be calculated from large amounts of data and then partitioned according to RPM and WOB, or more generally relative to an alternative drilling parameter set. Also, since one objective is to determine the amount of signal present at harmonics of the rotary speed, for a selected drilling parameter partition, it is appropriate to bin the data about each harmonic frequency. The bins at multiples of the rotary speed frequency allow for some signal variation and noise at each harmonic. The bins should be neither too wide nor too narrow to accomplish the objective of determining the amount of signal present for each harmonic, or alternatively for any other excitation frequency (such as mud pump excitation as previously noted). Those skilled in the art will understand that width selection is flexible and largely determined by application or analysis needs or scope, data set size, processing capabilities and needs, and the objective of the analysis.

Figure 2:
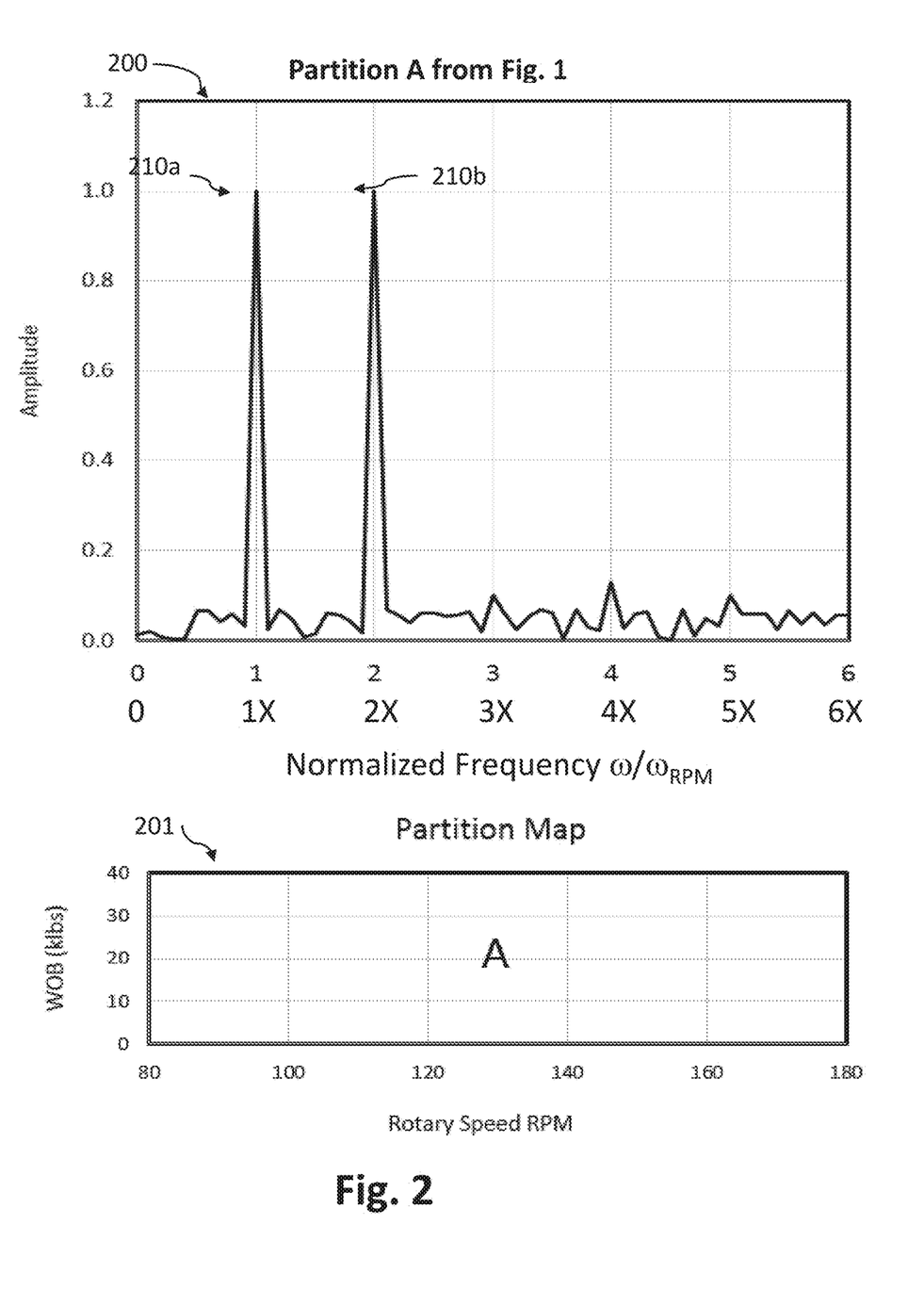
FIG. 2 illustrates another spectral response of a dataset wherein the entire dataset is processed together and includes a partition map corresponding to the selected range of the exemplary drilling parameters.

FIG. 2 illustrates a spectrum 200 for a single partition 201 of a dataset. The RPM range for the partition ranges from 80 to 180 RPM and there is no separate WOB partitioning. The single spectrum 200 shown in FIG. 2 has substantially equal peak amplitude for the 1× (210*a*) and 2× (210*b*) modes, with virtually no other excitation modes indicated.

Dataset partition selection points may be determined as desired for the problem at hand, using the limiting drilling parameters to determine partitions as deemed appropriate. As a non-limiting example, for a drilling operation having parameters for RPM from 60 to 150 RPM and WOB from 0 to 30,000 lbs., partitioning bins may be provided as 60-80, 80-100, 100-120, 120-140, and 140-160 RPM. Correspondingly, for WOB, the bins may be from 0-10,000, 10,000-20,000, and 20,000-30,000 lbs. Another WOB partition might be for 0-30,000 lbs., for which all the data is in one WOB bin. Also, the RPM bin may be from 0-200 RPM, for which all the drilling rotary speeds are in one partition. Both cases together would be a condition in which all the data falls into one partitioning bin.

In another example, the partitions might be related to ROP and RPM. As one example, the partition map might be divided by ROP because the interval might include hard and soft rock, so division into 0-30, 30-60, 60-90, and 90-120 ft/hr might be a good way to characterize the dataset. All RPM and WOB values could be included within these ROP partitions.

In yet another example, a particularly interesting condition might be for all WOB that exceed zero, i.e. for the drilling condition in which the bit is in contact with the formation. Another WOB partitioning might be for zero or negative WOB and some minimum rotary speed when the bit is off bottom, representing the condition of string rotation off bottom. These are mere examples and should not be considered to be limiting in any sense.

It is sufficient to say that data shall be obtained downhole and/or at surface from a drilling measurement system that has sufficient resolution in time and amplitude, capable of recording sufficient data quantities, such that it may be analyzed for its frequency content and represented numerically in such manner as to provide amplitude data for certain frequency bands of interest. This data may then be partitioned into individual datasets of drilling parameters for spectral analysis that might be deemed appropriate.

Figure 3:
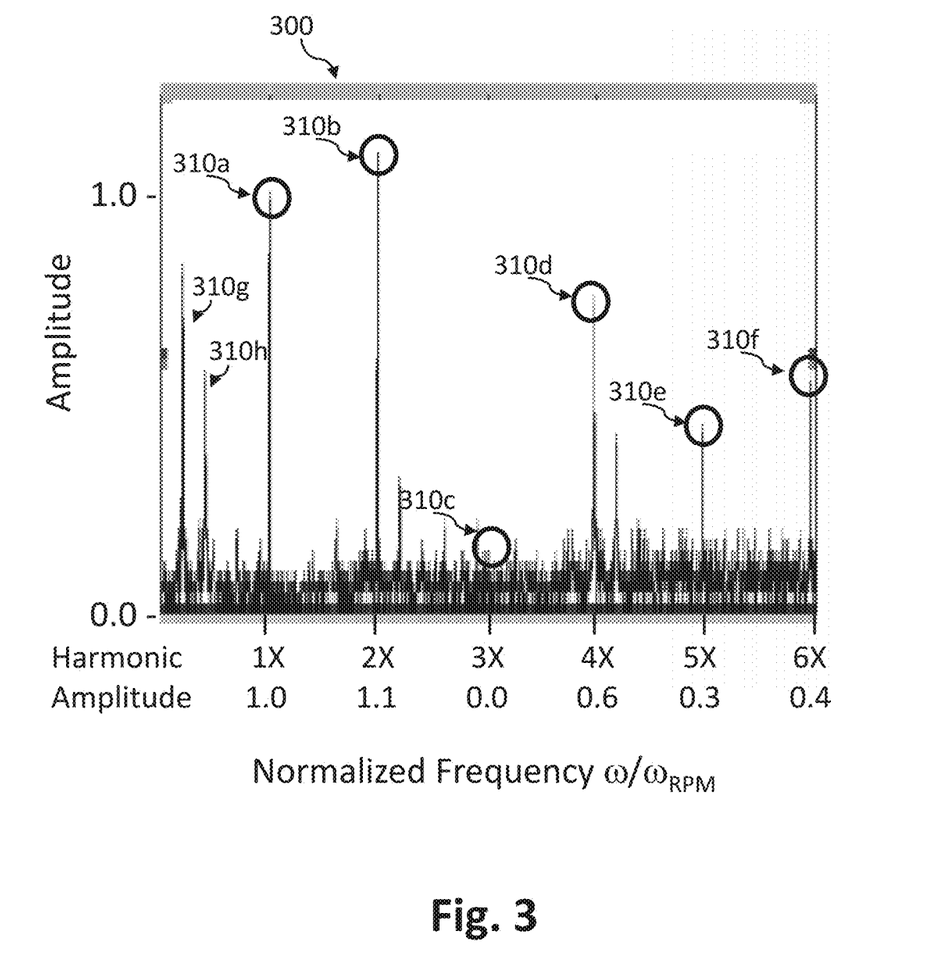
FIG. 3 is a spectral response of another dataset determined for a specific drilling parameter partition, wherein the different harmonics of the fundamental rotary speed are highlighted and the amplitude values at these harmonics are identified.

FIG. 3 is a spectral response of another dataset determined for a specific drilling parameter partition, wherein the different harmonics of the fundamental rotary speed are highlighted and the amplitude values at these harmonics are identified. Additional acceleration content that is most likely the result of fluid pressure variations while pumping are also identified in this chart. FIG. 3 illustrates a spectrum calculated for a dataset partition that includes drilling parameters RPM(i) and WOB(j). The normalized frequency is calculated as the frequency of this spectrum divided by the surface rotary speed (expressed in frequency units), resulting in a non-dimensional horizontal axis as seen in prior figures. This normalized frequency axis may then be subdivided into bins, at least including the integral multiples of the rotary speed (harmonic frequencies) and any other excitations of interest.

$$S = S(RPM, WOB, \omega) \quad \text{(Eqn. 2a)}$$

Thus for each drilling state, the respective spectra may be written with subscripts for the corresponding spectral bins corresponding to this drilling state, designated as the $i^{th}$ RPM, $j^{th}$ WOB, and $k^{th}$ frequency bin, wherein in one implementation a set of frequency bins may be selected to include the harmonics of the surface rotary speed but alternatively may also include other frequencies of interest.

$$S_{ijk} = S(RPM_i, WOB_j, \omega) \quad \text{(Eqn. 2b)}$$

FIG. 3 illustrates representative spectra (300) for a specific RPM and WOB partition. The data shows the following amplitudes for the respective multiples of the rotary speed: 1× mode, 1.0 (310a); 2× mode, 1.1 (310b); 3× mode, 0.0 (310c); 4× mode, 0.6 (310d); 5× mode, 0.3 (310e); and 6× mode, 0.4 (310f). These are identified as the spectral amplitudes in this example, for the binned RPM and WOB intervals corresponding to this dataset.

Note in passing that there is no limitation for application of this concept to the spectral peaks identified by peaks 310g and 310h in FIG. 3. These may occur at a frequency less than the rotary speed and are thought to be related to the mud pump stroke rate as mentioned above. This excitation source may be readily included in this process using additional bins and possibly multiple partitions of the drilling data.

Figure 4:
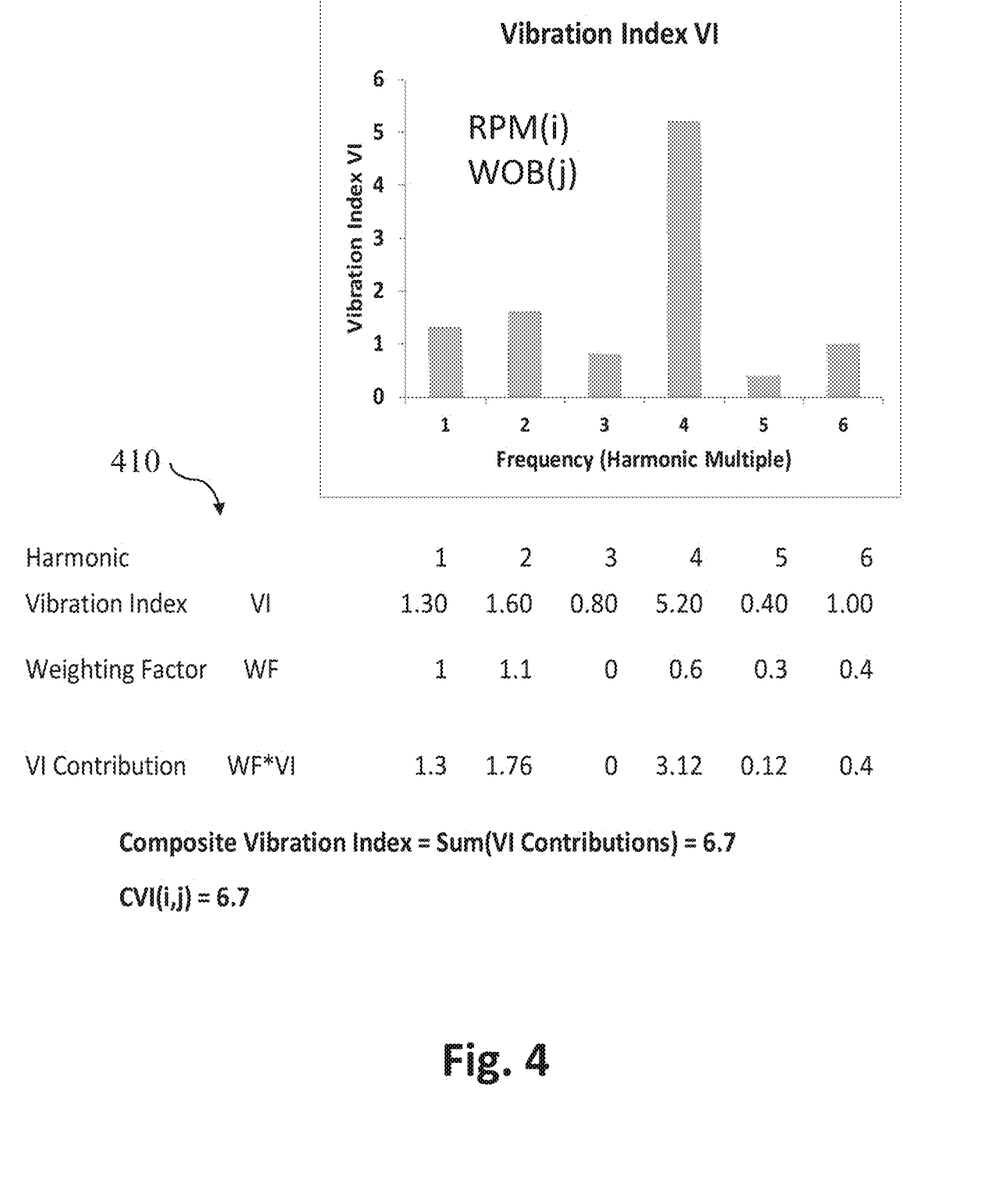
FIG. 4 shows an example of a vibration index chart comprised of model results for a specified drilling parameter set comprising weight on bit (WOB) and surface rotary speed (RPM) that are within the corresponding partition FIG. 5 provides an example of drilling parameters over a certain time and depth interval, to illustrate how different drilling data partitions may be configured.

FIG. 4 provides an example of a vibration index chart comprised of model results for a specified drilling parameter set comprising weight on bit (WOB) and surface rotary speed (RPM) that are within the corresponding partition map of the data of FIG. 3. Vibration index model results are identified at the harmonics (integral multiples) of the rotary speed. Below the chart, a table illustrates matching of the vibration index values with spectral weighting factors, which in this instance are taken to be the harmonic amplitudes of FIG. 3. The contributions of the vibration index for each harmonic times the spectral weighting factor are then shown. The total composite vibration index for this WOB and RPM is the sum of these contributions.

FIG. 4 depicts a vibration model result comprising the illustrated Vibration Index (VI) values 400 for a specific drilling parameter dataset, in this case comprising an RPM and a WOB value. Depending on the partitioning that is established for the problem at hand, there may be only one model result for a specific spectrum if the drilling parameter partitions are small. On the other hand, FIG. 3 could be the spectral result for an entire dataset comprising varying RPM and WOB, for which there would be many possible vibration model results 400 corresponding to the specific values provided in FIG. 4 for a particular drilling parameter set. Thus the mapping from calculated vibration index model results to the spectral maps of measured datasets may be one-to-one or it might be many-to-one. Alternatively, there may be a third case in which there are many spectra that correspond to a specific drilling parameter dataset and corresponding vibration model result, wherein each spectrum corresponds to a different drilling condition, for example different lithologies, different hole angles, different drilling tools, etc. A non-limiting example of this case may be an extensive dataset from one bit run.

The data table 410 illustrates one mathematical calculation to combine the vibration model results to form an exemplary Composite Vibration Index (CVI). In this example, each harmonic multiple is identified below the chart 400. The vibration index VI value is shown for each of the harmonics, calculated from the model for the specific drilling assembly and the specified RPM(i) and WOB(j) conditions.

Below the VI values are the weighting factors for each harmonic. For this case, the weighting factors are chosen to be the spectral amplitudes taken from FIG. 3, denoted by "WF" in FIG. 4. The contribution of each VI is calculated through multiplication and denoted by "WF*VI". Finally, the Composite Vibration Index is the sum of the contributions from each of the harmonic model results times the spectral weighting factor.

Figure 5:
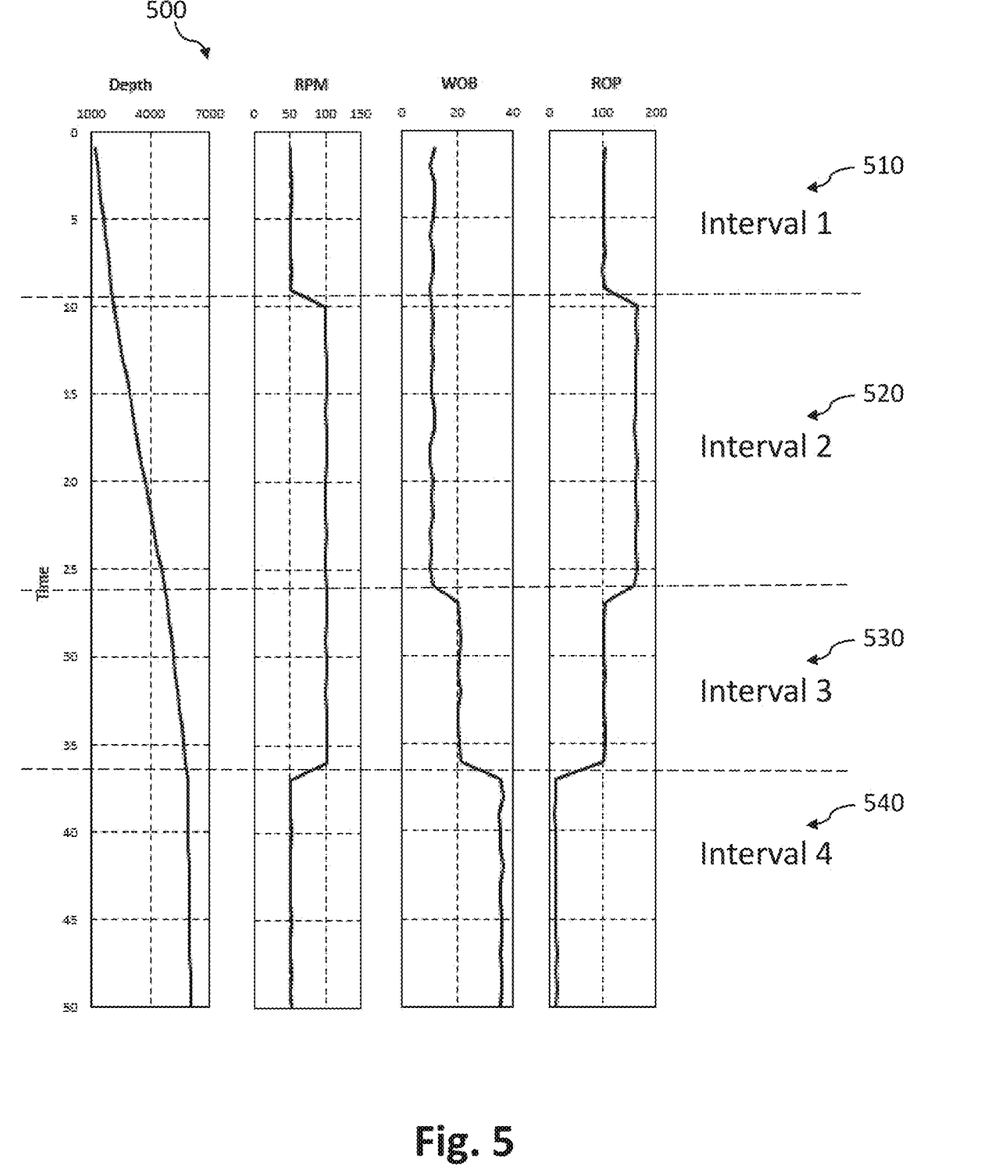

FIG. 5 illustrates a sample time and depth interval and associated drilling parameters. In the four intervals, the RPM and WOB change, and the resulting ROP varies as the parameters change and as the formation response, and likely drilling tool condition, changes over the section. Starting at the top, good ROP is established in Interval 1, but then the RPM is increased without appreciable change in WOB. The ROP increases commensurately, indicating no apparent change in lithology. In Interval 3, ROP declines even as WOB increases at constant RPM. The formation properties are now slightly harder and/or the drilling tools are beginning to dull. A significant decline in ROP is seen in Interval 4 as the RPM is reduced and the WOB is increased substantially. The formation resistance has now increased substantially and/or the drilling tools are now significantly dulled.

It may be appropriate to consider all of this dataset 500 as a single partition, and calculate one spectrum from the on-bottom drilling time of the entire dataset. Naturally, drilling connection time and other off-bottom data would be excluded from this data partition in the most likely case. On the other hand, each interval (510, 520, 530, and 540) could be considered its own partition, with individual spectra determined accordingly. In yet another case, Intervals 1-3 (510, 520, and 530) could be one partition and Interval 4 (540) a separate partition, on the basis of the significant apparent change in formation between these two sections.

It should be clear that there is no single means to partition the data, and that there are many different ways to partition the same dataset. For this reason, the concept of dataset partitioning within the context of this disclosure should be considered to be any representative subdivision of the data determined for a number of possible contributing factors. In addition, multiple partitioning arrangements may be applied within the same analysis.

Figure 6:
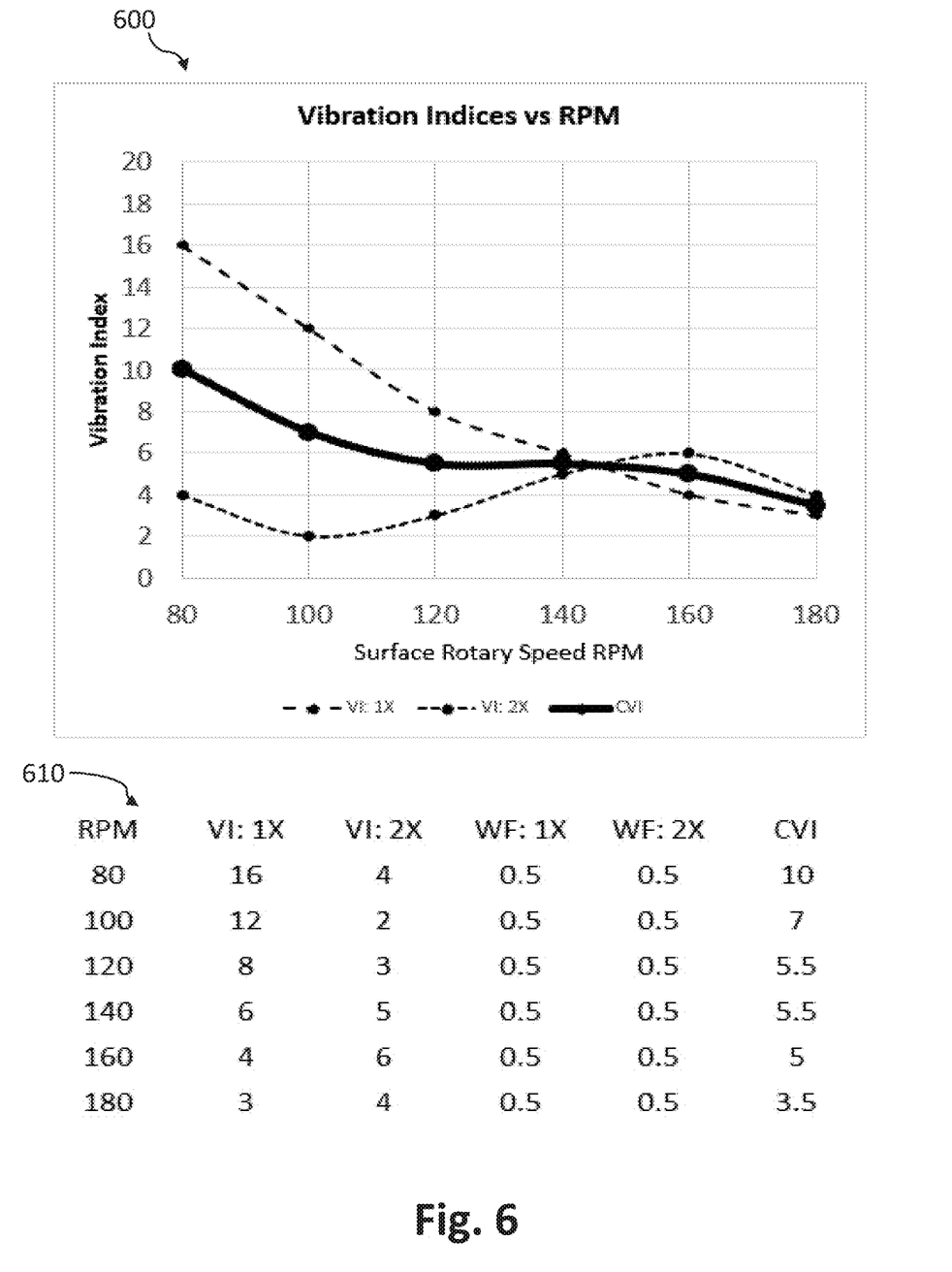
FIG. 6 illustrates the 1× (1-times) mode and 2× (2-times) mode vibration indices over a rotary speed range from 80 to 180 RPM for an exemplary drilling assembly.

FIG. 6 illustrates the 1× (1-times) mode and 2× (2-times) mode vibration indices over a rotary speed range from 80 to 180 RPM for an exemplary drilling assembly. In this non-limiting example, the spectrum of FIG. 2 illustrates that spectral weighting factors of 0.5 are to be applied to both the 1× and 2× harmonics (equal weights that sum to 1.0), and a Composite Vibration Index is thus calculated as the average of the indices for the two modes. Note that this example implies a weighting factor of zero for the 3×, 4×, and higher harmonic vibration modes.

FIG. 6 illustrates an exemplary CVI calculation data set 610 over multiple drilling parameters illustrated in chart 600. Consider that for a specific drilling assembly, model results are calculated for the fundamental 1× harmonic and the 2× harmonic for a specific WOB and 80 to 180 RPM. In FIG. 6, the 1× vibration index is the dashed line, and the 2× index is the dotted line. The spectrum of FIG. 2 extends over the drilling parameters from 80 to 180 RPM and for 0 to 40 klbs WOB as seen in the partition map FIG. 2. For convenience, the sum of the weighting factors may be taken to be one, so in this exemplary but non-limiting case the 1× and 2× harmonics each have a factor of 0.5. The CVI calculated for this example is illustrated as the heavy solid line in graph 600.

Compared to the VI determined by the 1× index by itself, the CVI that includes the 2× harmonic mode indicates that operating the drilling assembly at 120-140 RPM may be satisfactory, whereas this conclusion is contraindicated by the 1× result alone. Understanding the spectral content of measured data and calculating a Composite Vibration Index may provide better interpretation of frequency domain model results, thereby improving the operational guidance that may be provided to the driller.

Since the vibration magnitude in general varies in time, either the relative or absolute harmonic estimates, or both, may be considered in this analysis. Data may be processed for on-bottom drilling, off-bottom reaming, or both. Thus, there may be several such relationships for different methods to generate different spectral maps $S_{ijk}$ that vary chiefly in the types of normalization and averaging applied, and for different dynamic drilling measurements as well. In general, alternative statistical methods may be used to combine information for different spectral estimates $S_{ijk}$. For example, torsional data while back-reaming off bottom may be more severe than the on bottom drilling condition, for which the spectral values of the former are greater than those of the latter. Consequently, the inventive method may weight drill string design modeling results for the back-reaming condition with greater weighting factors than the design while drilling on bottom, if this operation cannot be avoided and is deemed important to the drilling process.

Although the spectral weighting factor may be selected to be proportional to the spectrum of any given measurement, for example an acceleration value, other weighting factors related to the spectral data may be utilized. Wherein c is a constant scaling factor of proportionality and ω is the frequency, three weighting factors may be written as follows, $$WF_{ijk} = c * S_{ijk}(RPM_i, WOB_j, \omega_k) \quad \text{(Eqn. 3a)}$$

$$WF_{ijk} = \left(\frac{c}{\omega}\right) * S_{ijk}(RPM_i WOB_j, \omega_k) \quad \text{(Eqn. 3b)}$$

$$WF_{ijk} = \left(\frac{c}{\omega^2}\right) * S_{ijk}(RPM_i, WOB_j, \omega_k) \quad \text{(Eqn. 3c)}$$

These non-limiting transforms of the spectrum of data measurements illustrate three possible spectral weighting factors calculated from the spectral data. For data measurements comprising acceleration, these equations may be interpreted in the following way. An acceleration spectrum (Eqn. 3a) will have higher amplitudes at higher frequencies, and an acceleration-based weighting will increase emphasis on the higher frequency modes of the vibration model result. On the other hand, a spectrum of the displacement (Eqn. 3c) will have relatively higher emphasis on the lower frequency modes of vibration. Spectral weights based on the velocity (Eqn. 3b) will yield a set of weights with intermediate emphasis on the higher frequencies.

Additional spectral transforms and mathematical combinations are contemplated. The spectral amplitude or the spectral magnitude (square of the amplitude) might be used in one instance, or the square root of the transformed spectral weighting factor using Eqn. 3c in another case. Many alternatives may be considered.

However so obtained from the measured data, a composite spectrum may be generated for a dataset partition. This spectrum may be a constant applied to all model applications, or it may vary over a number of different conditions, depending on the granularity of the drilling state partitions. These datasets may also be specific for a particular drilling assembly, or they may be applicable to many drilling assemblies.

Without loss of generality, a Composite Vibration Index (CVI) may be determined from the individual frequencies calculated by the model, using spectral weighting factors in the following way, for the $i^{th}$ RPM and $i^{th}$ WOB, $$CVI_{ij} = \Sigma_k WF_{ijk} VI_{ijk}(RPM_i, WOB_j, \omega_k) \quad \text{(Eqn. 4a)}$$

For an individual partition, the spectral weighting factors WF may be a function of the frequency only, and the composite vibration index simplifies to the following, $$CVI_{ij} = \Sigma_k WF_k VI_{ijk}(RPM_i, WOB_j, \omega_k) \quad \text{(Eqn. 4b)}$$

Although these relationships are shown as summations, they may in general be determined as an average value, such as a simple mean value, a root-mean-square (RMS) value, or some other means to combine each term to yield a composite vibration index that includes weighting of the component frequencies comprising the spectral weighting factors that are determined from field data measurements of a drilling assembly. The summation over frequency bins may be implemented alternatively as an integration, which may be preferred if considering the inclusion of frequency content that is not a harmonic of the rotary speed.

Figure 7:
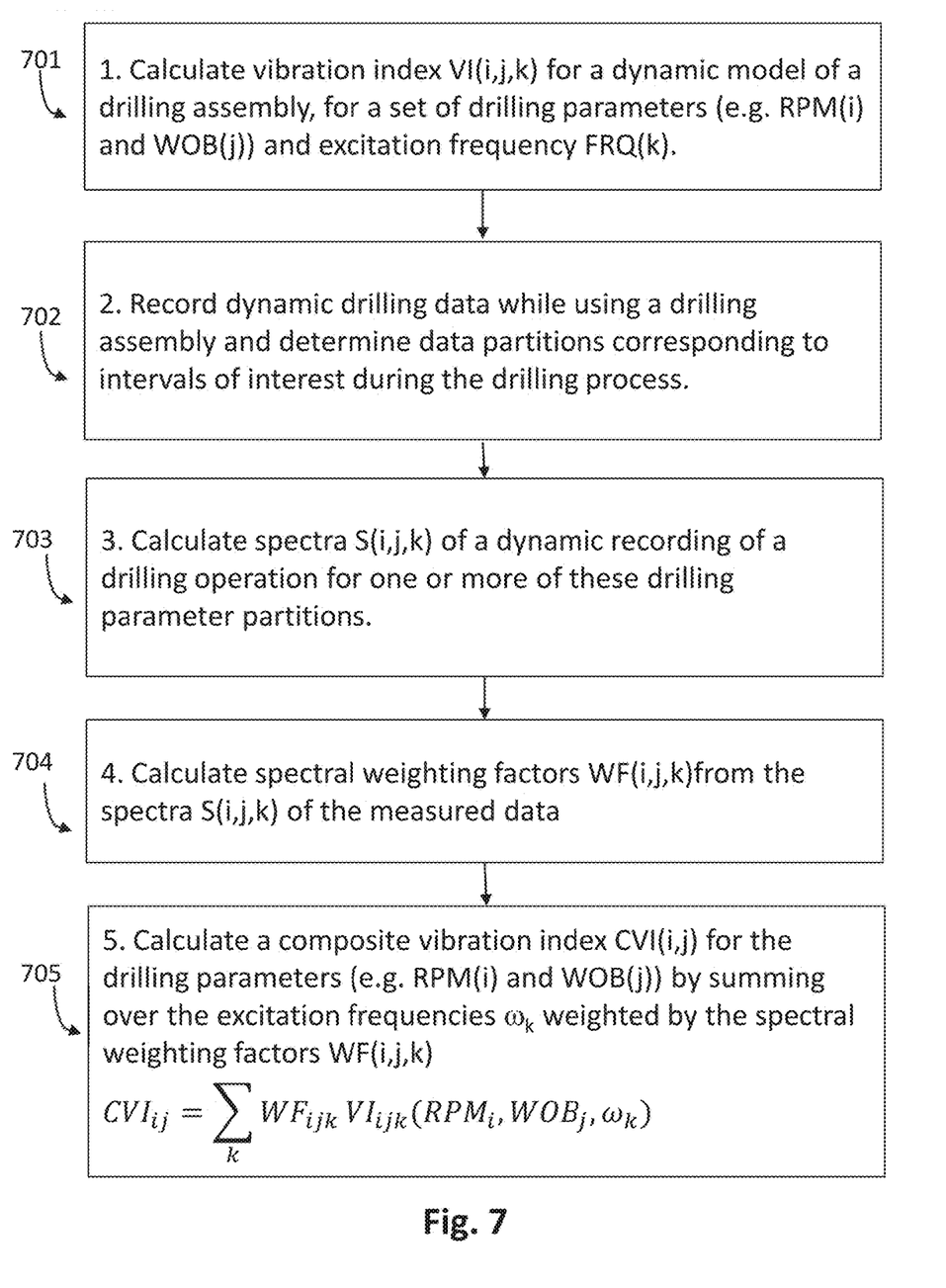
FIG. 7 is a generalized flowchart of this calculation process in which each step is identified. Excitation frequencies may include both integral harmonics as well as additional sources of excitation observed in the data.

FIG. 7 summarizes the process and illustrates one embodiment of the inventive method to apply spectral weighting factors to calculate Composite Vibration Indices using a frequency domain model of a drilling vibration and measured data to combine model results.

In Step 1 701 of FIG. 7, a frequency domain dynamic model is used to calculate model results over a drilling parameter range (e.g. RPM and WOB) for different excitation frequencies. In Step 2 702, record drilling data while using a drilling assembly. During this drilling process, one or more data partitions of interest may be identified, for reasons including those considered in the above discussion. A single partition may be used, or multiple partitions. Each of these partitions may have a spectrum of a data measurement determined in Step 3 703. From these spectral calculations, a transform may be applied to obtain spectral weighting factors corresponding to each partition of the data in Step 4 704. For each such partition and corresponding spectral weighting factors, for various drilling parameters that include RPM and WOB but may include other parameters (ROP, torque, drilling fluid rate or pressure, etc.), a Composite Vibration Index may be determined by applying the weighting factors to component vibration indices calculated for each drilling parameter and excitation frequency (Step 5) 705.

INDUSTRIAL APPLICABILITY

The systems and methods disclosed herein are applicable to the wellbore constructing industry, even more particularly to the oil and gas wellbore constructing industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

While the presently disclosed technology may be susceptible to various modifications and alternative forms, the exemplary embodiments discussed above have been shown only by way of example. However, it should be understood that the invention is not intended to be limited to the particular embodiments disclosed herein. Indeed, the presently disclosed inventions include all alternatives, modifications, and equivalents falling within the true spirit and scope of the invention as defined by the following appended claims.

We claim:

1. A computer implemented method to drill a borehole within a subterranean formation with a drilling assembly, the method comprising the following steps:
   selecting a lateral, torsional, or axial mode frequency-domain dynamic model of the drilling assembly, wherein the dynamic model describes a dynamic response of the drilling assembly to excitation at an excitation frequency for operating at a set of selected drilling parameters that include at least a rotary speed and a weight on bit;
   providing a non-transitory machine-readable storage medium having stored thereon a routine of set instructions for using the selected frequency-domain model and for causing the machine to perform one or more of the steps of;
   calculating the dynamic response of the dynamic model for an excitation of the drilling assembly for at least two excitation frequencies for each of at least two sets of selected drilling parameters;
   calculating vibration indices from the calculated dynamic model response to represent the system output for each of the at least two excitation frequencies for each set of drilling parameters;
   receiving data measurements from at least one drilling operation that includes measurements pertaining to the excitation of the selected dynamic model;
   identifying drilling parameters in the measured dataset that correspond to the selected model drilling parameters;
   determining drilling parameter partitions of the data measurements for the selected drilling parameters;
   calculating at least one frequency domain spectrum of the data measurements for each of the partitions;
   determining for each of the partitions, from the at least one calculated frequency domain spectrum, spectral weighting factors based at least on the spectral amplitude at each of the two or more excitation frequencies in the at least one spectrum;
   calculating a composite vibration index by combining the calculated vibration indices for each excitation frequency with the spectral weighting factors for each of the drilling parameter partitions;
   displaying said composite vibration index for each of the drilling parameter partitions;
   selecting preferred drilling parameters based on the displayed results;
   and
   using the preferred drilling parameters to drill a borehole with the modeled drilling assembly.

2. The method of claim 1 wherein spectral weights are determined for at least two partitions of drilling operating parameters.

3. The method of claim 1 wherein the drilling operating parameters include at least rotary speed and drilling rate of penetration.

4. The method of claim 1 wherein the drilling operating parameters include at least rotary speed and surface drilling torque.

5. The method of claim 1 wherein the spectral weights are constant values determined for a plurality of combinations of rotary speeds and bit weights for which the cutting fact of the drill bit is in contact with the formation and making new hole.

6. The method of claim 1 wherein the spectral weights are determined for the condition when a cutting face of the drill bit is rotating off bottom.

7. The method of claim 1 wherein the excitation frequencies comprise a fundamental harmonic frequency that is synchronous with the rotary speed of the drilling assembly and at least one harmonic multiple thereof.

8. The method of claim 1 wherein at least two drillstring assemblies are modeled and the results are displayed for each modeled drillstring assembly, wherein one drilling assembly is selected based on the model results, and further wherein the selected drilling assembly is used to drill a borehole.

9. The method of claim 8 wherein the same spectral weighting factors are used for each model of the at least two drilling assemblies.

10. The method of claim 8 wherein at least two different spectral weighting factors are used for each of the models of the at least two drilling assemblies.

\* \* \* \* \*